United States Patent [19]

Thompson

[11] Patent Number: 4,949,720
[45] Date of Patent: Aug. 21, 1990

[54] APPARATUS FOR MEASURING THE LEAD CURRENT IN A PACEMAKER

[75] Inventor: David L. Thompson, Fridley, Minn.

[73] Assignee: Medtronic, Inc., Minneapolis, Minn.

[21] Appl. No.: 246,600

[22] Filed: Sep. 20, 1988

[51] Int. Cl.$^5$ ............................................. A61N 1/37
[52] U.S. Cl. .......................... 128/419 P; 128/419 PG
[58] Field of Search ...... 128/419 P, 419 PG, 419 PT, 128/419 R, 709, 697, 696

[56] References Cited

U.S. PATENT DOCUMENTS

| | | | |
|---|---|---|---|
| 4,141,367 | 2/1979 | Ferreira | 128/419 PT |
| 4,142,533 | 3/1979 | Brownlee et al. | 128/419 PT |
| 4,332,256 | 6/1982 | Brownlee et al. | 128/419 PT |
| 4,337,776 | 7/1982 | Daly et al. | 128/419 PT |
| 4,354,498 | 10/1982 | Weigert et al. | 128/419 R |
| 4,414,979 | 11/1983 | Hirshorn et al. | 128/419 F |
| 4,498,478 | 2/1985 | Bourgeois | 128/419 PG |
| 4,594,565 | 6/1986 | Barreras | 128/419 PG |
| 4,649,931 | 3/1987 | Beck | 128/708 |
| 4,697,591 | 10/1987 | Lekholm et al. | 128/419 PT |
| 4,706,674 | 11/1987 | Dieken et al. | 128/419 R |
| 4,811,738 | 3/1989 | Economides et al. | 128/419 PG |
| 4,827,933 | 5/1989 | Koning et al. | 128/419 PG |

OTHER PUBLICATIONS

Technical Manual "Medtronic 8329 Pasys Pulse Generator", Nov. 1985, MC 841725a.

Primary Examiner—Lee S. Cohen
Assistant Examiner—Kennedy J. Schaetzle
Attorney, Agent, or Firm—Reed A. Duthler; John A. Rissman

[57] ABSTRACT

Pacer lead current is assessed by monitoring the current through one of a plurality of output stage transistors.

4 Claims, 3 Drawing Sheets

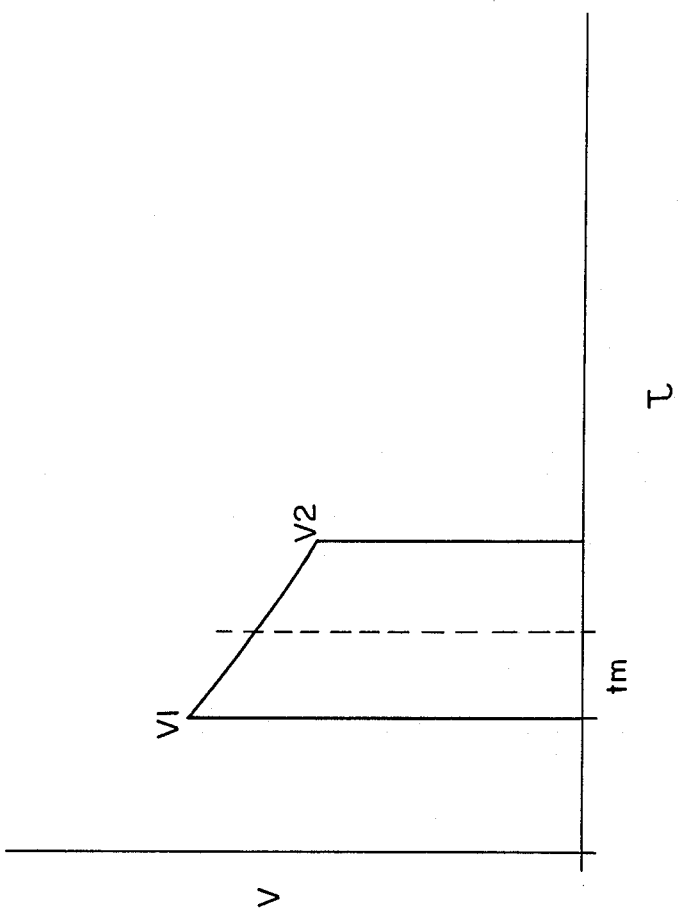

APPARATUS FOR MEASURING THE LEAD CURRENT IN A PACEMAKER

FIELD OF THE INVENTION

The present invention relates generally to implantable pacemakers and more particularly to an output circuit topology which permits the measurement of output current to the heart.

BACKGROUND OF THE INVENTION

Implantable pacemakers are coupled to the heart through a lead system. In operation, the pacemaker periodically provides an electrical output stimulus which is delivered to the complex impedance of the heart. The amount of energy delivered to the heart depends on the resistance of the lead and the heart tissue. It has been routine to measure this impedance or threshold at the time of implantation to permit optimizing the location of the pacing lead and to maximize longevity of the pacer. These acute measurements are made with an oscilloscope or, more frequently, with a special instrument called a pacing system analyzer or PSA.

Later, after the lead has "healed" into the heart tissue, the margin of capture and delivered energy are estimated by the physician. With the advent of output pulse programmable pacers, physicians have been able to adapt the pacer's output to the threshold requirements of the patient and thus prolong the longevity of the implanted device.

To assist the physician with followup care, modern pacers use internal circuitry to monitor the output pulse parameters and to telemeter this information to the physician via a programmer. This information is used in assessing the performance of the pacemaker and the associated lead.

A problem which is presented by this technology is a discrepancy between the measured values of lead current and delivered energy presented by the programmer, PSA and oscilloscope. These differences result primarily from different measurement methodologies.

Typically, prior art pacers place a series resistor in the output path of the lead current. During the delivery of a pacing stimulus, the voltage drop across the resistor is measured and telemetered out. This technique requires the use of a high precision resistor to reduce measurement errors. It also introduces a component whose failure can lead to an undesirable "no output" condition. Also, such a system is wasteful of output energy because of the inclusion of the measuring resistor.

SUMMARY OF THE INVENTION

In contrast to this prior art, the present invention includes a large number (typically 200) of FET transistors operated in parallel to discharge a capacitor though the heart tissue. Pacer lead current is monitored by measuring the current through a small number (typically 2) of these transistors.

The current monitoring function is performed by a current-to-voltage converter coupled to an analog-to-digital converter which may make one or more voltage measurements during the output pulse. The ability to time the measurement with respect to the leading and trailing edges of the output pulse provides flexibility to match the telemetered pacing current data with operating room measurements thus reducing the confusion that discrepancies can cause.

Additionally, the voltage developed by the current-to-voltage converter may be applied through additional circuitry to the gates of the FETS to provide for a constant current output pulse.

BRIEF DESCRIPTION OF THE DRAWINGS

FIG. 3 is a waveform diagram of a typical pacer output pulse.

DESCRIPTION OF THE PREFERRED EMBODIMENT

Figure 1:
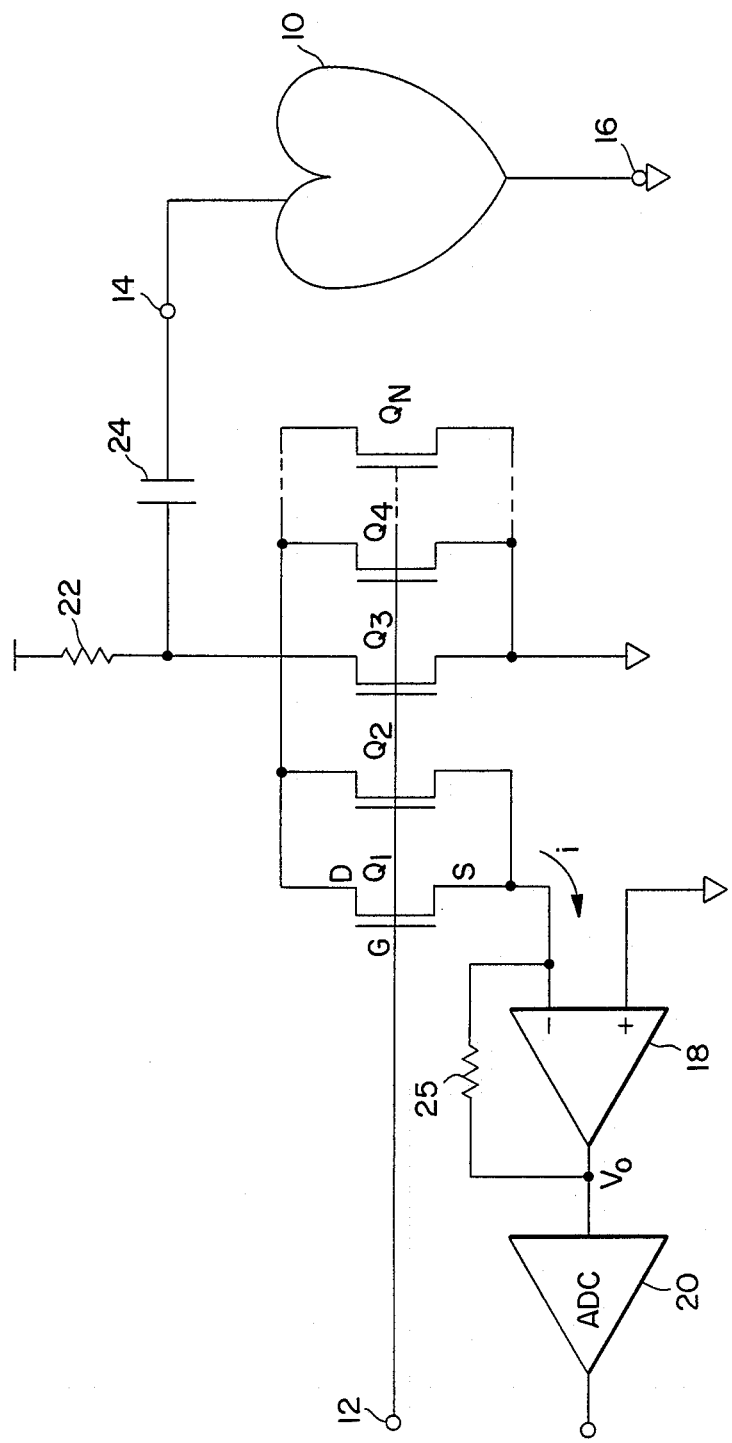
FIG. 1 is a schematic diagram of an illustrative embodiment of the present invention.
Figure 2:
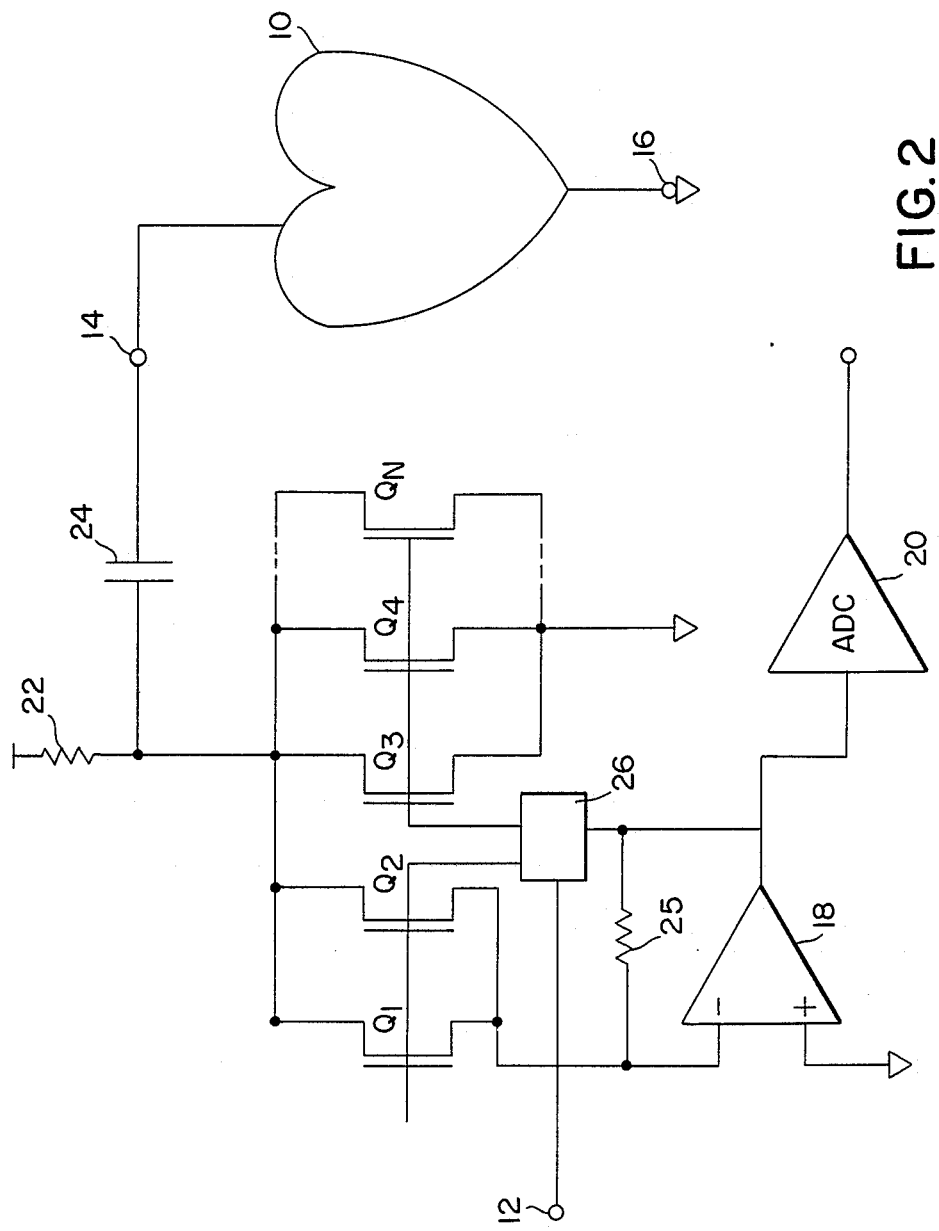
FIG. 2 is a schematic diagram of an alternate embodiment of the present invention.

The circuitry depicted in FIGS. 1 and 2 show simplified pacer output circuits wherein like numerals are used to identify like components.

A logic level pace signal generated by pulse generator logic (not shown) is coupled to terminal 12 to initiate an output pulse. The output pulse is coupled to the heart 10 via a conventional lead system which may include a conventional tip electrode and a case or ring electrode.

At the conclusion of the output pulse shown in FIG. 3, the recharging resistor 22 will recharge the output capacitor 24 through the heart 10.

The control voltage present at terminal 12 is distributed to the gates of the number of monolithic FET transistors. These voltage controlled devices divide the output current and share it. Within the constraints of die topology and geometry, each FET is identical and therefore shares the output current equally. One or more of the transistors from the array are selected for connection to current monitoring circuitry. The current flow in these sampling transistors reflect the total current delivered by the array. Illustrative circuitry for monitoring current may include an operational amplifier 18 coupled to an analog to digital converter 20. In operation, the drain source current is converted to a voltage by the operational amplifier 18 and resistor 25 (where $V_{out} = -i \times R$). This voltage may be converted to a binary number by the analog-to-digital converter. The value of the current measurement may be transmitted to a remote or external receiver. The external instrument converts the telemetered information to a measurement of output current, lead impedance or output pulse energy.

The waveform generated between the output terminal 14 and circuit ground 16 connected to the heart load 10 is depicted in FIG. 3.

The output pulse shown in FIG. 3 will occur as the output capacitor 24 is discharged through the current limiting impedance of the heart 10 and the array of drain source resistance of output transistors. The duration of the output pulse corresponds to the "on" time of the transistors.

The voltage on the capacitor 24 declines exponentially from an initial voltage V1 to a final voltage V2 during the "on" time of the transistors. The difference in the voltages is proportional to the load present at the output terminal 14.

The time at which the output current is monitored TM is selected such that the current measured displayed to the physician will conform to the value measured by other equipment. This calibration technique assumes that the lead impedance is constant, and therefore the concomitant instantaneous output current is linearly proportional to the instantaneous output voltage. In this instance, the current measurement made when the output voltage is V1 will be higher than the current value when the measurement is made when the output voltage is V2.

It should also be apparent that one could make a current measurement at both the V1 and V2 voltage and compute an arithmetic average output current. Likewise a measurement at V1 would give peak values. A measurement at a fixed time after V1 (TM =90 microseconds) would indicate values similar to commonly available pacing system analyzers.

Additionally, as shown in FIG. 2, the output voltage of the operational amplifier derived from the sampling transistor current flow can also be used as a control voltage to drive the gates of output transistors to provide a constant current output through gate control circuitry 26. In operation, the operational amplifier 18 output is biased to a nominal drive voltage corresponding to the desired drain source current for the output transistors shown in the figure as Q1, Q2, Q3, Q4 and QN. If the current delivered to the load by the array is low due to increased lead impedance, the control voltage at the output of the operational amplifier will increase the gate voltage to increase the drain/source current of the array transistors thus regulating the output current to the desired level.

What is claimed is:

1. In a pacemaker having output circuit means for generation of stimulation pulses, timing means for triggering said output circuit means to provide said stimulation pulses, and terminal means coupled to said output circuit means for providing said stimulation pulses to said heart, the improvement wherein:

said output circuit means comprises an output capacitor and switching means for providing current flow between said output capacitor and said terminal means in response to said timing means, said switching means comprising a plurality of parallel connected metal oxide semiconductor output transistors; and wherein said pacemaker further comprises measuring means coupled to at least one of said output transistors for monitoring the drain to source current of said at least one of said output transistors, when current flows between said output capacitor and said terminal means.

2. A pacemaker according to claim 1 wherein said measuring means comprises a current to voltage transducer connected between the source of said at least one of said output transistors and a reference potential.

3. A pacemaker according to claim 2 wherein said measuring means further comprises an analog-to-digital converter coupled to a voltage output of said current to voltage transducer whereby the current monitored through said at least one of said output transistors is converted to a number.

4. A pacemaker according to claim 2 or claim 3 wherein a voltage output of said current to voltage transducer is supplied to the gates of said output transistors to regulate the gate voltage of said output transistors to control the drain/source current of said output transistors.

* * * * *